(12) United States Patent
Kusano

(10) Patent No.: US 6,508,647 B2
(45) Date of Patent: Jan. 21, 2003

(54) PASTE FORMULATION FOR DENTAL USE, A PASTE INJECTOR, AND A SYSTEM FOR DETECTING OF PASTE FILLING

(76) Inventor: Kazunori Kusano, Room 207, Hanamizuki-shinkan, 4-7, Mahikizawa 2-chome, Tamashi, Tokyo 206-0023 (JP)

( * ) Notice: Subject to any disclaimer, the term of this patent is extended or adjusted under 35 U.S.C. 154(b) by 0 days.

(21) Appl. No.: 09/930,080

(22) Filed: Aug. 15, 2001

(65) Prior Publication Data

US 2002/0045148 A1 Apr. 18, 2002

Related U.S. Application Data

(62) Division of application No. 09/529,145, filed as application No. PCT/JP99/03975 on Jul. 26, 1999.

(30) Foreign Application Priority Data

Aug. 30, 1998 (JP) .......................... 10/260908
Aug. 31, 1998 (JP) .......................... 10/259115

(51) Int. Cl.[7] ................................................ A61K 6/04
(52) U.S. Cl. ............................ 433/81; 433/32; 433/72
(58) Field of Search ........................... 433/32, 81, 224, 433/72, 80

(56) References Cited

U.S. PATENT DOCUMENTS 3,000,805 A * 9/1961 Carritt et al.
3,078,850 A * 2/1963 Schein et al.
3,674,012 A * 7/1972 Sage
3,682,162 A * 8/1972 Colyer
3,916,529 A * 11/1975 Mousseau
3,919,775 A * 11/1975 Malmin
4,269,174 A * 5/1981 Adair
4,447,206 A * 5/1984 Ushiyama .................... 433/27
4,515,168 A * 5/1985 Chester et al.
4,944,678 A * 7/1990 Villette ........................ 433/224
5,306,236 A * 4/1994 Blumenfeld .................. 604/21
6,293,944 B1 * 9/2001 Ellman et al. ................ 606/41
6,356,783 B1 * 3/2002 Hubbard, Jr. ................ 600/546

FOREIGN PATENT DOCUMENTS

WO    WO 87/00029    * 1/1987

* cited by examiner

*Primary Examiner*—Ralph A. Lewis
(74) *Attorney, Agent, or Firm*—Bachman & LaPointe, P.C.

(57) ABSTRACT

A paste formulation for dental use, a paste injector, and a system for detecting paste filling are disclosed. The paste formulation includes electric conductive material. The present invention also discloses the system for detecting paste filling comprising a paste injector (1) containing electric conductive paste (D) and an electric conductive member for electrically connecting the electric conductive paste (D) to an external electrode, a current detector (101) for detecting the current flowing through the electric conductive paste (D) reserved in the container portion (1), and a current display device (105) for indicating the current flowing through the electronic conductive paste (D).

4 Claims, 9 Drawing Sheets

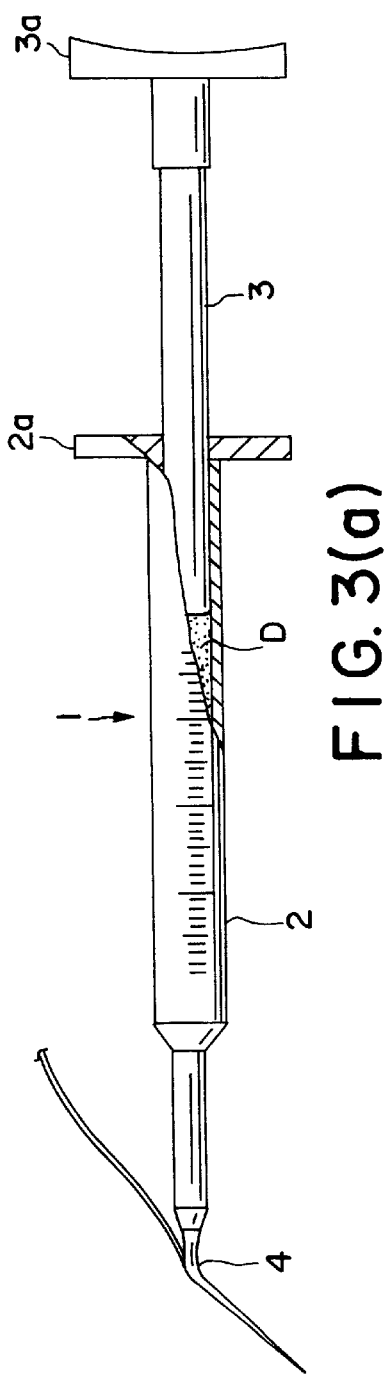
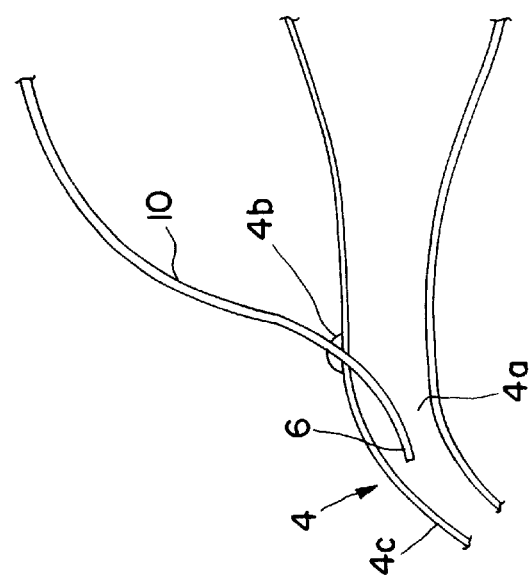
FIG. 3(a)
FIG. 3(b)

US 6,508,647 B2

PASTE FORMULATION FOR DENTAL USE, A PASTE INJECTOR, AND A SYSTEM FOR DETECTING OF PASTE FILLING

This is a Division, of application Ser. No. 09/529,145, filed Apr. 5, 2000, which is a 371 of PCT/JP99/03975, pending filed Jul. 26, 1999.

FIELD OF INVENTION

The present invention relates to a paste formulation, a tool, and a system for root canal treatment, more particularly relates to the paste used for root canal filling, a paste injector, and a system used therewith.

BACKGROUND ART

In dental clinical treatments, root canal treatments are popularly operated. Among the root canal treatments, root canal filling is the stage operated at the final stage of the root canal treatment, and then the root canal filling has large effects on prognosis of a damaged tooth. Since the length to an apical constriction varies from individual patients, a length of the root canal must be measured. A method for this measurement includes, conventionally to measure an actual length of the tooth by using a reamer, a file, or a scale as detection probes for an x-ray photograph. Recently, a method for measurement of the root canal length using an impedance is widely used, because there is a case that the x-ray exposure is not adequate for a pregnant woman and the impedance measurement is speedy and provides exact results.

The root canal length measurement by the impedance conventionally uses a root canal meter etc. A working length is then determined to be the reamer length inserted in the root canal minus 1 mm which is indicated by a predetermined impedance previously measured depending on a conditions of the instruments for measurement when a top of the reamer contacts to the periodontal membrane. Alternatively, the working length is determined as the length that gives current or resistance being different by a certain value from the value which indicates contact to the periodontal membrane.

A root canal filling material, or root canal filling agent such as a filler paste formulation conventionally used for the root canal filling includes a gutta percha point used together with various sealers, silver points and a filler in a paste formulation which may be formulated with a sustainable disinfectant or an accelerator for healing with osteoid scar.

Especially, a method for filling the paste formulation in the root canal portion includes filling the paste formulation through the reverse-rotated reamer operated by hand, filling by using a filling device with a helical shape such as Rentulo plugger, or filling the paste through a paste injector. However, the methods using the reamer and Rentulo plugger have disadvantages, because these methods require an extra procedure for measuring the root canal length and the special device.

FIG. 9 shows a conventional method for filling the paste formulation into the root canal by the injector. In the conventional root canal filling method using the injector, the injector 1 shown in FIG. 9(a) filled with the paste formulation M is used. The injector 1 comprises a container portion 2 and an insert portion 3 which may be inserted into the container portion 2. A tube for injection of the filler is disposed to a front end of the container portion 2 to form an injection portion 4. In FIG. 9(a), the tip of the paste injection tube is inserted into the root canal portion which has previously been spread widely.

In the conventional root canal filling method, as shown in FIG. 9(b), the paste formulation M is injected into the root canal while inserting the filler injection tube into the root canal and pressing the insert portion 3 in the direction of the allow A. When the filling is completed, the filler injection tube is drawn out from the root canal and then the root canal filling operation is completed.

When the root canal is filled by the injector, as described above, an advantage to complete the injection easily and quickly may be provided without the procedure to measure the root canal length previously. However, this method has yet some disadvantages, that is, filling of the paste to the apical constriction is unknown and the paste formulation may irritate root peripheral tissues when the paste formulation is injected beyond the apical constriction. When the filling is not enough, a dead space and/or residual pulps may be allowed to exist. Therefore, there are needs for the paste formulation, the paste injector, and the system for detecting the paste filling.

DISCLOSURE OF THE INVENTION

In the first aspect of the present invention, a paste formulation for dental use comprising electronic conductive material may be provided.

In the first aspect of the present invention, the paste formulation is provided, wherein the electronic conductive material is powder.

In the first aspect of the present invention, the paste formulation for dental use may be provided, wherein the electronic conductive material is selected from the group consisting of metal powder, metal oxide powder, coated inorganic powder by metal and/or doped metal oxide, carbon powder, carbon whisker, and whisker integrated with metal.

In the first aspect of the present invention, the paste formulation for dental use may be provided, wherein the paste formulation includes at least one compound selected from the group consisted of calcium hydroxide, hydroxy apertite, tricalcium phosphate.

In the first aspect of the present invention, the paste formulation for dental use may be provided, wherein the paste formulation includes at least one compound selected from the group consisting of iodoform, barium sulfate, anhydrous zinc sulfate, aluminum sulfate, and zinc oxide.

In the first aspect of the present invention, the paste formulation for dental use may be provided, wherein the paste formulation includes at least one vehicle selected from the group consisting of silicone oil, guaiacol formaldehyde mixture, propylene glycol, dry ethanol, caster oil, liquid paraffin.

In the first aspect of the present invention, the paste formulation for dental use may be provided, wherein the paste formulation includes at least one compound selected from the group consisting of iodoform, barium sulfate, anhydrous zinc sulfate, aluminum sulfate, and at least one vehicle selected from the group consisting of silicone oil, guaiacol-formaldehyde mixture, propylene glycol, dry ethanol, caster oil, and fluid paraffin.

In the first aspect of the present invention, the paste formulation for dental use may be provided, wherein the paste formulation includes an x-ray contrast agent.

In the first aspect of the present invention, the paste formulation for dental use may be provided, wherein the electronic conductive material is present between 5~50 wt % based on a solid of the paste formulation.

In the first aspect of the present invention, the paste formulation for dental use may be provided, wherein the paste formulation includes at least one compound selected from the group consisting of calcium hydroxide, hydroxy apertite, tricalcium phosphate not less than 30 wt % based on a solid of the paste.

In the second aspect of the present invention, a paste injector may be provided. The paste injector comprises;

a container portion within which electric conductive paste is reserved, an insert portion inserted into the container portion, an injection portion for injecting the electric conductive paste formulation into a constricted portion portion, and an electric conductive member for electrically connecting the electrically conductive paste formulation to an external electrode.

In the second aspect of the present invention, the paste injector may be provided, wherein the electric conductive member comprises a terminal exposed at an end face of the insert portion inserted into the paste container portion and contacting to the electric conductive paste formulation, a terminal disposed at the insert portion and exposed outside the insert portion, and a lead line connecting between the terminals.

In the second aspect of the present invention, the paste injector may be provided, wherein the electric conductive member is inserted through the insert portion.

In the second aspect of the present invention, the paste injector may be provided, wherein the electric conductive member comprises an end extending through an inner path of the injection portion, an end drawn out of the paste injector, and a lead line connecting between the ends.

In the third aspect of the present invention, a system for detecting paste filling may be provided. The system comprises;

a paste injector comprising an electric conductive paste formulation and an electric conductive member for electrically connecting the electric conductive paste to an external electrode, a current detector for detecting the current flowing through the electric conductive paste formulation injected into a constricted portion, and a current display device for indicating the current flowing through the electronic conductive paste.

BRIEF EXPLANATION OF DRAWINGS

FIG. 3 shows a second embodiment of the paste injector according to the present invention;

BEST MODE FOR CARRING OUT THE INVENTION

Figure 1:
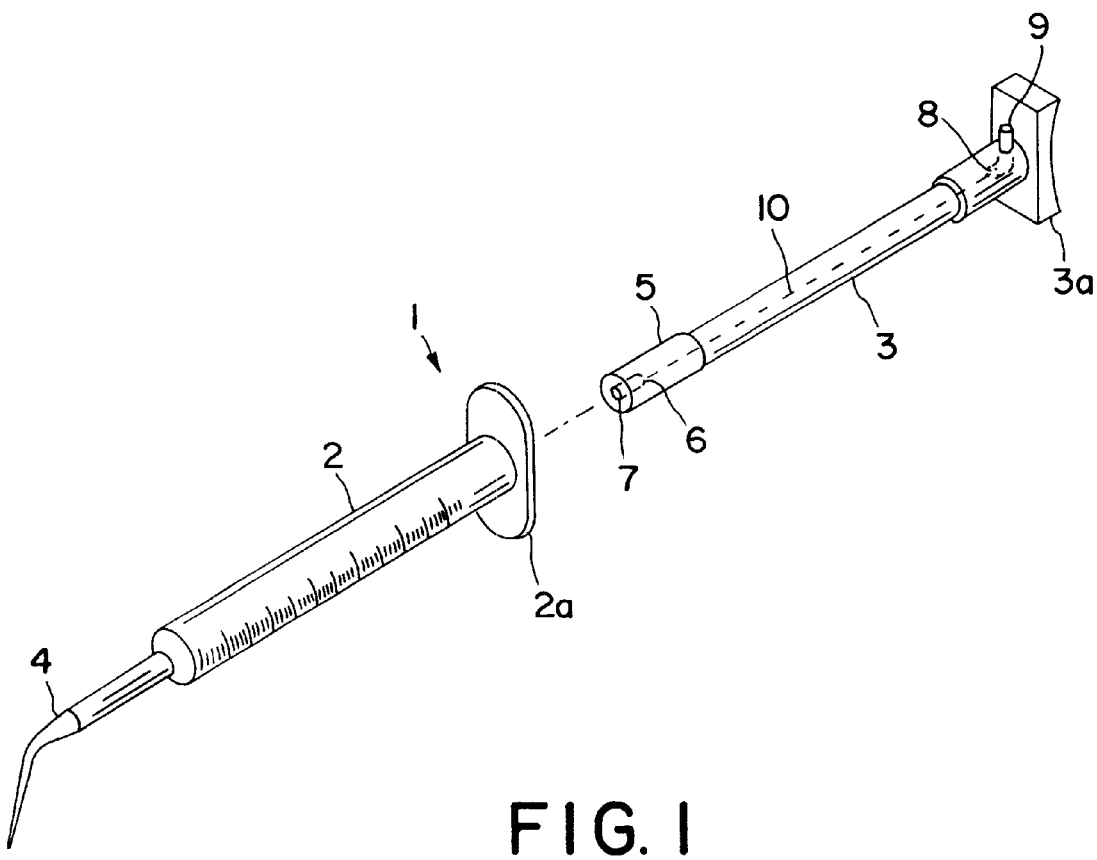
FIG. 1 shows the paste injector according to the present invention.
Figure 2A:
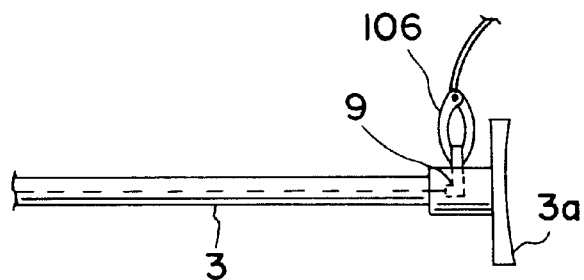
FIG. 2 shows details of the paste injector according to the present invention.
Figure 2B:
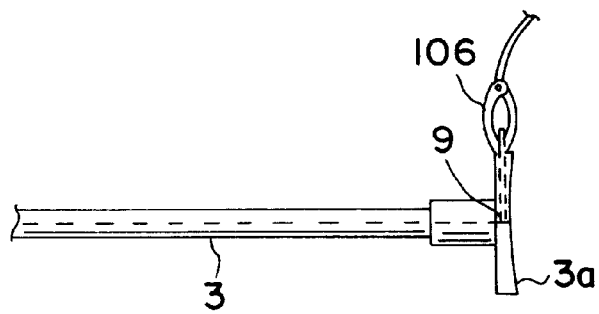
Figure 2C:
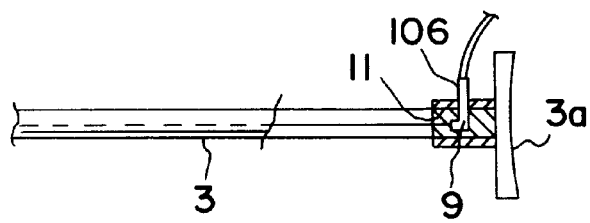
Figure 2D:
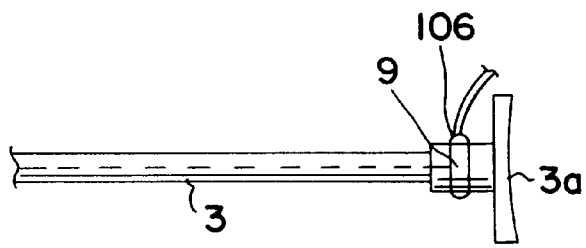

The present invention provides an electric conductive paste formulation for the dental treatment, i.e., an electric conductive paste formulation, a paste injector, and a system for detecting paste filling. Hereafter, the electric conductive paste formulation, the paste injector, and the system for detecting paste filling will be described using the drawings attached when necessary.

The electric conductive paste formulation according to the present invention may be formulated by mixing a suitable electric conductive material to conventional compositions for forming of calcium hydroxide paste, zinc eugenol pasta, iodoform paste, paraform-formaline paste. These conventional paste compositions may include Triozinc pasta which is a mixture of paraform aldehyde, anhydrous zinc sulfate, aluminum sulfate, potassium sulfate, zinc oxide mixed with cresol, phenol, and creosote; Kri 1 which is a mixture of iodoform powder, para-chrolophenol camher, menthol, lanolin, glycerin; Carbitar which is a mixture of iodoform powder, calcium hydroxide powder, sulfathiazole powder, guanofuracin with a vehicle such as T-caine and guanofuracin; Bitapex which is a mixture of calcium hydroxide powder and iodoform powder with silicone: oil; FR which is a mixture of calcium hydroxide powder, zinc oxide powder, barium sulfate powder, and a vehicle such as guaiacol-formaldehyde mixture, propylene glycol, dry ethanol, caster oil, liquid paraffin; Sealapex which comprises a polymer resin and calcium hydroxide.

Other paste formulation such as Endofil which uses a polymeric material as a base and the paste formulations which use hydroxy apatite or tricalcium phosphate may be useful, because such paste formulations exhibit affinity to live tissues and accelerate hard tissues formation. These paste formulations may provide advantages that the formulation may be absorbed by the tissues if the paste formulation runs out from the apical constriction. The above described calcium hydroxide, hydroxy apatite, tricalcium phosphate may be included in the electric conductive paste in an amount not less than 30 wt %, more preferably not less than 50 wt % based on the weight of solid contents in the electric conductive paste formulation.

The electric conductive material suitably used in the present invention may include electric conductive powder so as to be mixed sufficiently with the above described paste formulations. Such electronic conductive powder may have a particle size between 200 Å~100 µm, more preferably, between 0.01~80 µm, most preferably between 10~50 µm in order to achieve a good filing performance. Shapes of the electric conductive powder may be a spherical shape, a needle shape, and a scale shape.

The powder may include metal powder such as, for example, gold powder, silver powder, copper powder, nickel powder, metal oxide powder such as, for example, ZnO, $SnO_2$, $I_2O_3$, ITO, various doped metal oxides such as antimony doped $SnO_2$, $BaSO_4$ coated with metal, $SnO_2$, or other electric conductive materials, $TiO_2$ powder coated by Ag, $TiO_2$ powder coated with $SnO_2$, electric conductive carbon black, powder having high aspect ratio such as, for example, potassium titanate whisker coated thereon by Ag or Pd, whisker coated thereon by $SnO_2$, electric conductive carbon whisker. Particularly, needle type powder may provide an improved volume resistivity of the electric conductive paste formulation with low contents.

The above described electric conductive paste may have volume resistivity from $10^{-2}$ Ωcm to $10^6$ Ωcm, and it is preferred that the resistance of the electric conductive paste formulation when injected in the root canal portion may exhibit resistance in an order of the resistance through the periodontal membrane. As described below, if the volume resistivity is too high, the detection of the paste injection may not provide sufficiently exact results.

The electric conductive powder may be present in the electric conductive paste formulation so as to provide the required volume resistivity to the electric conductive paste formulation, and the powder may present from 5 wt %~50 wt % based on the solid of the paste formulation, more preferably present from 10 wt %~30 wt % based on the solid of the paste formulation.

The vehicles may present in the electric conductive paste formulation from 10 wt %~70 wt %, more preferably from 30 wt %~60 wt %.

Hereinbelow, an exemplary embodiment of the paste formulation including calcium hydroxide as its major component and electric conductive metal powder will be explained.

First, calcium hydroxide is prepared. This calcium hydroxide may be used under the specification of Japanese Pharmacopoeia having the particle size from 10~50 μm.

In this electric conductive paste, iodoform may preferably be present, because an anti-bacterial activity may be extremely enhanced, and an x-ray imaging performance may be also improved.

In addition, the vehicle described above such as silicone oil etc. may be added to calcium hydroxide. Addition of the silicone oil may provide an anti-corrosion property to the paste formulation as well as providing an adequate flow performance.

Other additives to the calcium hydroxide may be selected from various types. For example, when x-ray contrast agents including bismuth bicarbonate, bismuth sulfate, zirconium silicate may improve the x-ray imaging performance of the paste.

A dispersion method for the powder may be selected from any well-known conventional dispersion methods. Especially, when the electric conductive powder having the particle size between 10 and 50 μm is used as described above, it is possible to apply various mixing and/or dispersion methods, because aggregation of the powder may not be so severe. In the preparation of the electric conductive paste formulation according to the present invention, the paste formulation may be prepared, for example, by providing a paste formulation which is premixed with calcium hydroxide, iodoform, and silicone oil, adding the electric conductive powder, mixing the resulted paste formulation again to formulate the electric conductive paste formulation, then filling the resulted electric conductive paste formulation into the injector in a form of a cylinder for use when necessary. However, it is possible to mix a non-conductive powder such as calcium hydroxide and the electric conductive powder together with the vehicle such as silicone oil at the same time so far as the paste formulation according to the present invention may be obtained.

In the above described embodiment, the conductivity/resistiyity described above may be obtained by adding electric conductive powder such as gold, silver, copper, and nickel having the particle size described above. Since the electronic conductivity is provided with the paste formulation, and the paste formulation may be injected into the root canal by an injector implemented with an electric conductive member, the adequate injection of the paste formulation to the root canal may be proofed by detecting the resistance. Further, since the electric conductive powder is added in the paste, and the thermal and electronic conductivities of the paste are improved so that good thermal and electric feelings may be obtained. When the carbon powder is used, it is expected to absorb formaldehyde included in form-cresol which is used to treat the root canal and is also included as the major component of form-cresol.

Referring to figures, an embodiment of the paste injector, which is able to inject the electric conductive paste formulation into the root canal and simultaneously to measure the electric resistance, will be explained in detail.

FIG. 1 shows an exploited view of a first embodiment of the paste injector 1 according to the present invention. The paste injector 1 comprises the container portion 2 for reserving the electric conducting paste formulation, the insert portion 3 being inserted into the container portion 2, the injection portion 4 formed as a tapered tube toward the tip and disposed at the front end of the container portion 2, and the seal member 5 disposed at the end of the insert portion 3 which is inserted to the container portion 2.

The container portion 2 and the insert portion 3 may be made of glass, or synthetic resin such as polypropyrene, polycarbonate, polyvinyl chloride. However, when a handling performance such as damage is considered, the portions 2, 3 may preferably be made of a synthetic resin such as polypropyrene, polycarbonate, polyvinyl chloride. The container portion 2 has a hollow inside portion within which the electric conductive paste formulation is reserved. The container portion 2 comprises a projection 2a at the end opposite to the injection portion 4 with which insertion of the insert portion 3 is made easy when fingers are rest thereon. Materials for forming the injection portion 4 may be selected from any materials as far as the shape of the tapered tube of the injection portion 4 is formed to be thin and flexible.

The insert portion 3 is used to extrude the electric conductive paste formulation reserved in the container portion 2. The seal member 5 disposed at the front end of the insert portion 3 improves the seal between the inner face of the container portion 2 and insert portion 3. Installation of the seal member 5 to the insert portion 3 may be achieved through various methods including engaging the seal member 5 in the shape of pipe onto a recess formed to the insert portion 3, or molding the seal member 5 made of a synthetic resin integrally around the insert portion 3.

At the end of the insert portion 3 opposite to the end inserted into the container portion 2 comprises the projection 3a extending beyond the diameter of the insert portion 3 so as to make the inset easy by exerting force by fingers when the electric conductive paste formulation is injected into the root canal. The projection 3a may be formed separately from the container portion 3 and then may be adhered by some types of adhesives as well as being integrally formed with the container portion 3.

When the electronic conductive paste formulation is injected into the root canal, the above described paste injector 1 is held by one hand, and clipping the projections 2a, 3a between the fingers to exert the force to extrude the electric conductive paste formulation into the root canal.

As shown in FIG. 1, the first embodiment of the insert portion 3 of the paste injector 1 according to the present invention is implemented with the conductive member. The conductive member comprises the end 6, the terminal 7, the end 8, the terminal 9, and the lead line 10 extending between the end 6 and the end 7. These components forms the conductive member by the end 6 being connected to the terminal 7 formed on the side of the seal member 5 which contacts to the electric conductive paste formulation. Another end 8 is connected to the terminal 9 extending outside the insert portion 3 from the position adjacent to the projection 3a formed on the insert portion 3. The lead line 10 extends through the insert portion 3, thereby the electric conductive paste formulation being connected electrically outside the insert portion 3. The lead line 10, the terminals 7, 9 may be implemented by insert molding when the insert portion 3 is molded, or by inserting them after molding thereof.

Figure 9A:
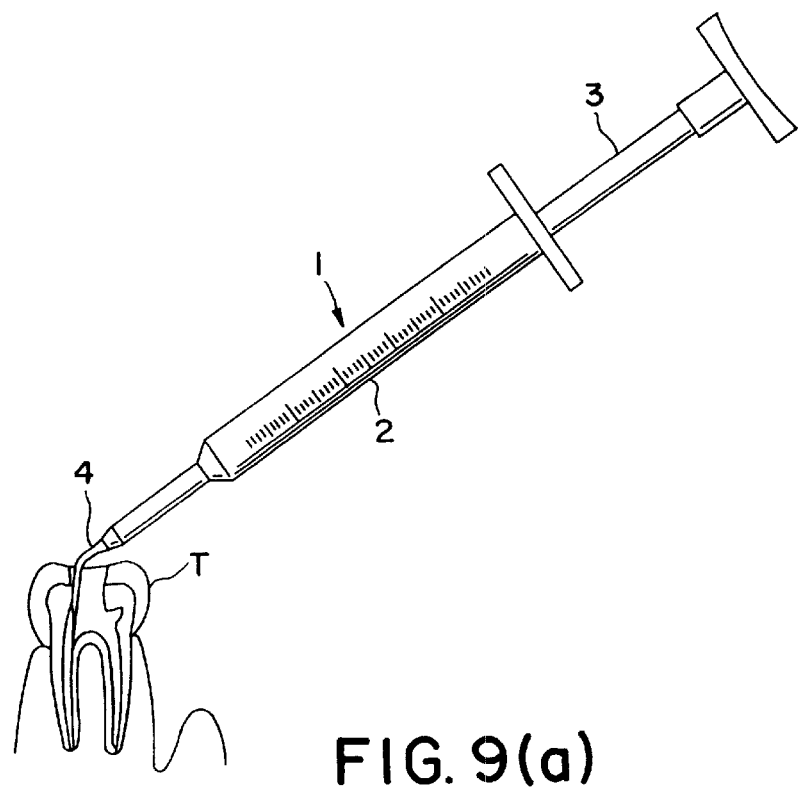
FIG. 9 shows a conventional root canal filling method by a conventional injector.
Figure 9B:
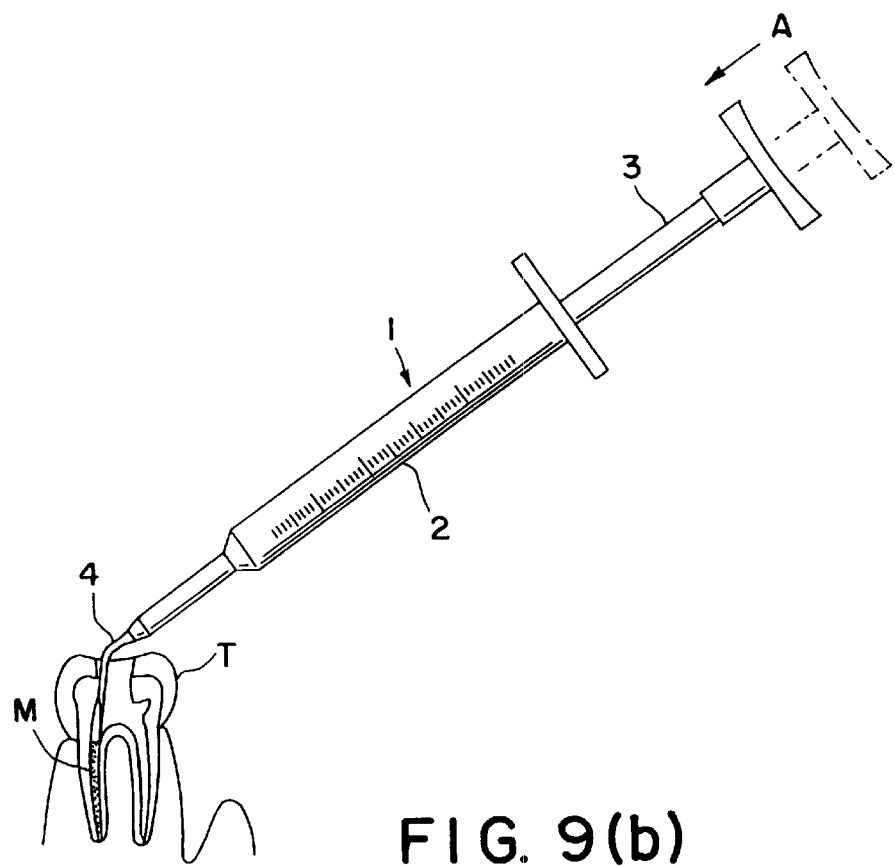

FIG. 2 shows an enlarged cross section of the terminal connecting portion of the terminal 9 of the first embodiment of the paste injector 1 according to the present invention. FIG. 2(a) shows an enlarged cross section of the insert portion 3 comprising the terminal 9. As shown in FIG. 9(a), the terminal 9 extends outside the insert portion 3 from the position adjacent to the projection 3a and the electrode 106 is connected to the terminal 9 through the clip. FIG. 2(b) shows that the terminal 9 is disposed in the projection 3a, and protrudes outside the insert portion 3 from the lateral side of the projection 3a. FIG. 2(c) shows that the terminal 9 has the opening 11 facing outside the insert portion 3 into which a needle electrode may be inserted or screwed. FIG. 2(d) shows that the terminal 9 is formed as the band which extends circumferencially and radially about the insert portion 3 at the position adjacent to the projection 3a of the insert portion 3. The arrangement of the terminal 9 illustrated in FIG. 2 may be selected depending on easiness of handling and operation for the root canal filling, and the constructions shown in FIG. 2 may be used in any combinations each other.

FIG. 3 shows a second embodiment of the paste injector 1 according to the present invention. FIG. 3(a) shows a partial cut away cross section of the paste injector 1, and the paste injector 1 comprises the container portion 2, the insert portion 3 which is inserted into the container portion 2. The injection portion 4 is formed to the tapered tube and is disposed at the front end of the container portion 2. In FIG. 3(a), the container portion 2 is partly cut away to show the electronic conductive paste formulation D. In the injection portion 4 of the paste injector 1 of the second embodiment according to the present invention, the lead line 10 extends outside the paste injector 1 at about the curved portion thereof so that distance between a tip of the injection portion 4 and the end of the lead line 10 may be substantially decreased with respect to the first embodiment so as to reduce adverse effects of the resistance of the electric conductive paste formulation D on the resistance measurement.

In FIG. 3(b), an enlarged cross section of the curved portion of the injection portion 4 attached to the paste injector 1 is shown. The second embodiment of the paste injector 1 shown in FIG. 3(b) has the lead line 10 extending through the inside path 4a adjacent to the tip from the lead line inlet position formed at the injection portion 4 as close as possible such that the end 6 may be located adjacent to the tip from which the electric conductive paste D is injected. When such construction is adopted, the distance between the end 6 and another electrode 104 (not shown) through the electric conductive paste formulation D may be reduced, thereby reducing the effect on the resistance measurements due to the resistance of the electric conductive paste formulation D.

When the lead line 10 is drawn out of the paste injector 1 of the second embodiment according to the present invention, the terminals 9 shown in FIG. 2 may be used. Alternatively, without providing the terminal 9, the lead line 10 is stripped at the both ends to obtain sufficient conductivity such that one end is disposed in the inner path 4a. Another end may be drawn outside the wall of he injection portion 4c while maintaining seal performance with a heat-seal or the adhesive 4b. It is of course possible to mold the lead line 10 integrally when the injection portion 4 is molded. The lead line 10 drawn out of the paste injector 1 may be extended to the projection 2a formed to the container portion 2 along to the outer lateral side so as not to contact the stripped end to an oral cavity, and thereafter be connected to an electrode of the apparatus for measuring resistance. The lead line used may have any thickness. However, to obtain good handling performance while not degrading the injection through the injection portion 4, the lead line 10 may preferably be thin sufficiently. The lead line 10 may have a cover, or may not have a cover.

Figure 4:
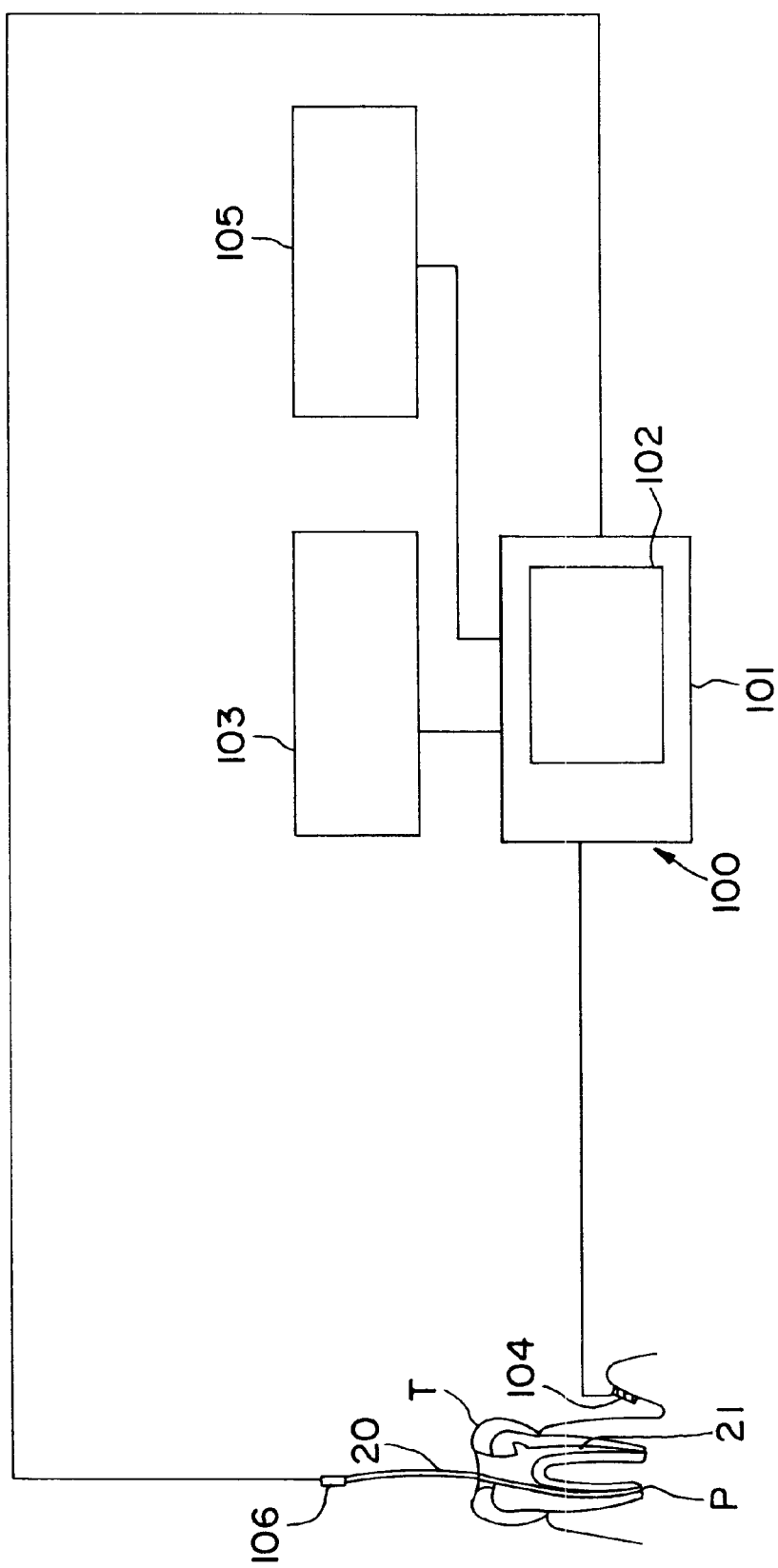
FIG. 4 shows an arrangement of a conventional system for impedance measurement used for detecting the working length.

Now, a system for detecting the paste filling will be explained hereinbelow with referring to FIG. 4~FIG. 7. FIG. 4 shows a conventional arrangement of a system for measuring the root canal length by the resistance or the impedance. When the root canal length is measured by the resistance conventionally, the operation thereof comprises steps of; first spreading the root canal portion of the damaged tooth T, next cleaning the spread root canal 21 by hydrogen peroxide while remaining hydrogen peroxide within the root canal 21, and then inserting the reamer 20 into the root canal 21.

The resistance measuring device 100 comprises the current detector 101, the power supply 102, the control device 103 including relay circuit, the electrode 104 connected to the damaged tooth through lip, the current display device 105 including a current indication device and/or an alarm device, and the electrode 106 connected to the end of the reamer 20. The resistance measuring device 100 actuates the current display device 105 through the control device 103 based on the current signal detected by the current detector 101. The resistance measuring device 100 acknowledges to the operator that the resistances or the current values become a predetermined values, or the top of the reamer reaches to the apical constriction P, or the top of the reamer reaches to the position having a predetermined distance, i.e., about 1 mm from the apical constriction P.

Figure 5:
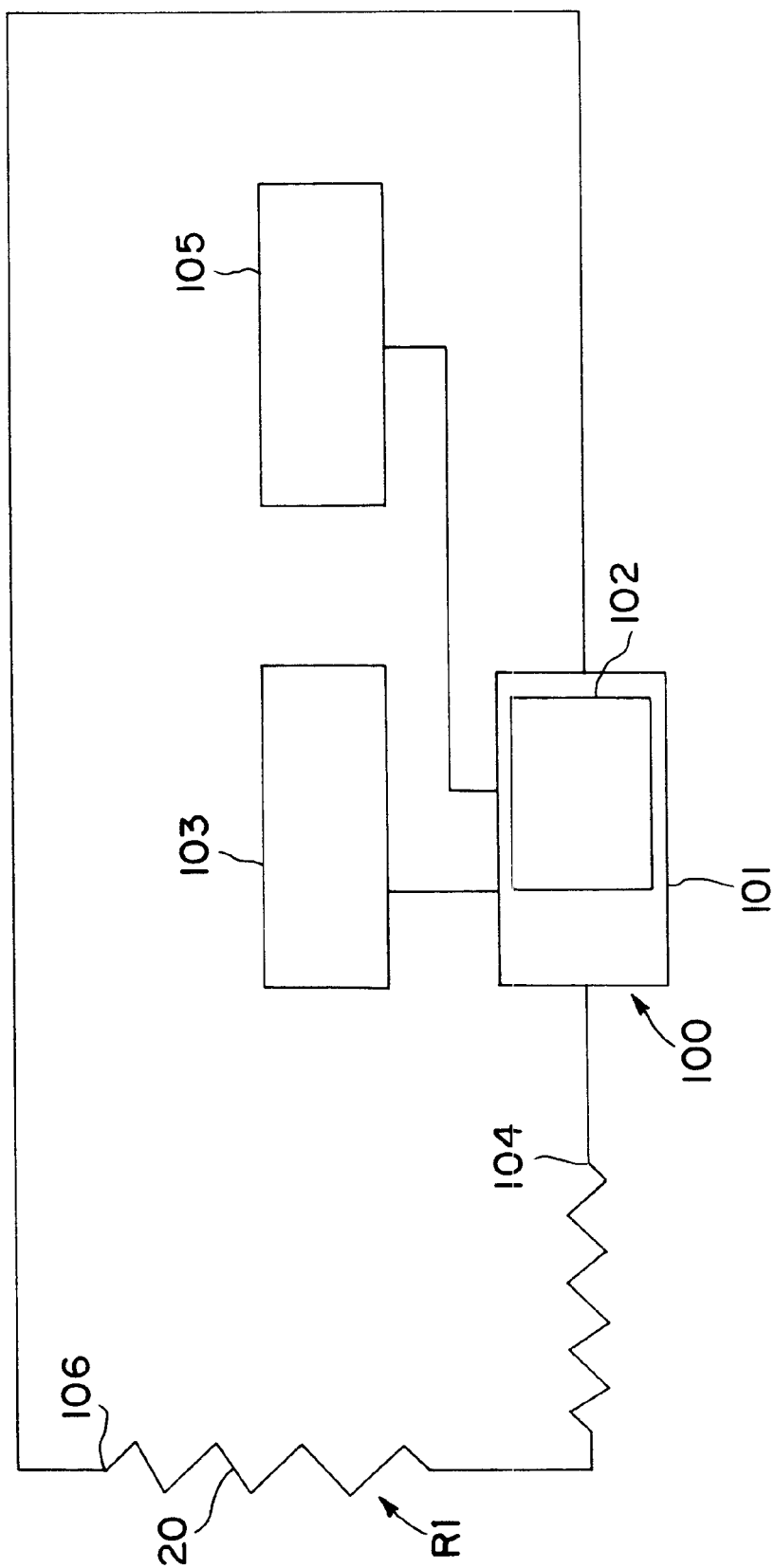
FIG. 5 shows a method for the root canal length measurement using the reamer and the impedance.

Usually, when the reamer 20 reaches to the periodontal membrane, the electric circuit formed between the reamer 20 and the electrode 104 which is connected to a tube contacting to a lip and being extended from a dental pump has a resistance about 6.5 kΩ including an internal resistance of the system for resistance measurement. FIG. 5 shows a schematic illustration of the resistances. In FIG. 5, the resistance of the reamer 20 is shown by the reference numeral R1. As shown in FIG. 5, the reamer 20, the periodontal membrane, and the electrode 104 usually connected to the dental tube form an electric circuit including a resistance R1. Usually, the inside of the root canal in which the reamer 20 is inserted is cleaned and is almost dried under the measurement. Therefore, the current may not substantially flow in the circuit. However, the current becomes to flow due to effects of exudate, and/or conductivity of hydrogen peroxide used in the cleaning process and remained therein as the top of the reamer 20 moves toward the periodontal membrane. When the reamer 20 reaches to the periodontal membrane, the entire circuit resistance becomes to the above explained resistance of about 6.5 kΩ.

The present invention uses the electric conductive paste formulation D as a probe electrode rather than using the reamer 20 as the probe electrode for the measurement of the root canal length.

Figure 6:
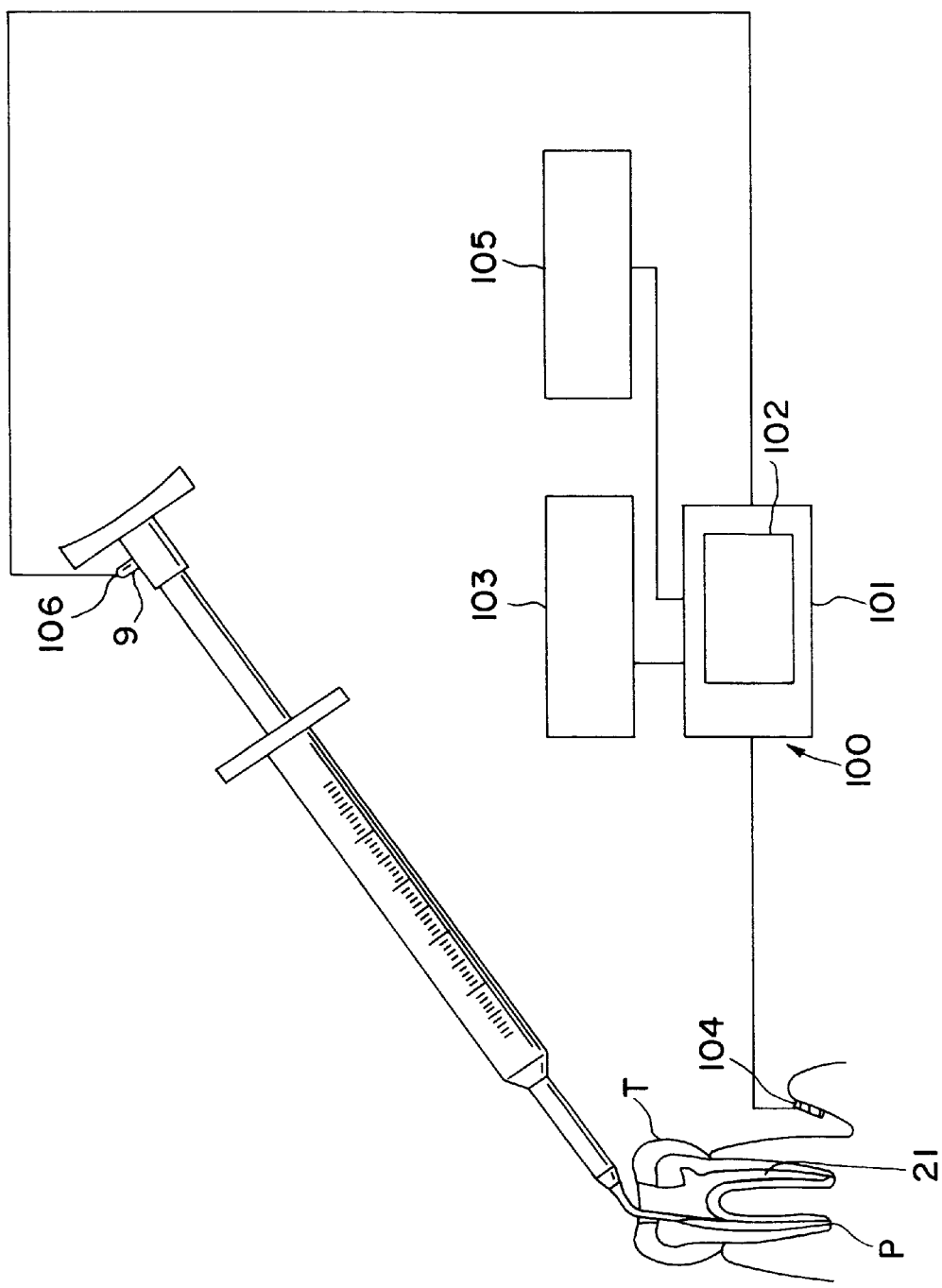
FIG. 6 shows an arrangement for filing electronic conductive paste D into the root canal of the damaged tooth by the paste injector of a first embodiment according to the present invention.

FIG. 6 shows an arrangement when the electric conductive paste formulation is filled in the root canal 21 of the damaged tooth T using the paste injector 1 according to the first embodiment of the present invention. As shown in FIG. 6, the terminal 9 is connected to the electrode 106 of the resistance measurement device 100, and the electrode 104 of the resistance measurement device 100 is connected to the dental tube. In the condition illustrated in FIG. 6, no current, or very low current flows through the current detecting device 101, and then the resistance is held high.

Figure 7:
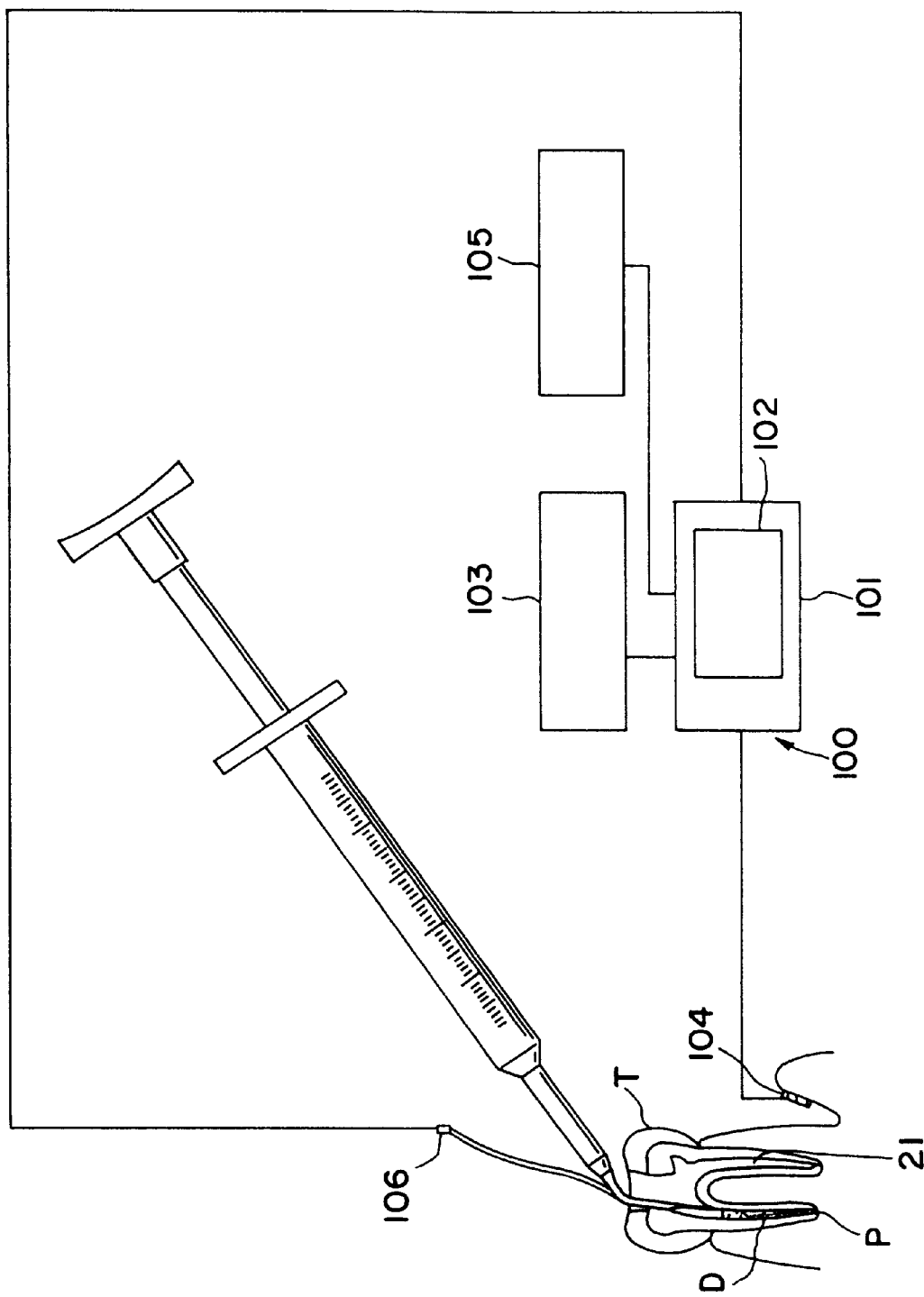
FIG. 7 shows an arrangement for filing electronic conductive paste D into the root canal of the damaged tooth by the paste injector of a second embodiment according to the present invention in the same arrangement shown in FIG. 6.

FIG. 7 shows the filling process of the electric conductive paste formulation D into root canal 21 using the same arrangement shown in FIG. 6 while the paste injector 1 according to the second embodiment of the present invention being used. As shown in FIG. 7, as the filling of the electric conductive paste formulation proceeds and the electric conductive paste formulation D becomes closer to the apical constriction P, a week current start to flow through the electric conductive paste formulation D. Finally the electric conductive paste D contacts to the periodontal membrane, and then the resistance R1 of the reamer 20 is replaced to the resistance R2. The resistance R2 depends on the distance between the position where the lead line 10 contacts to the electric conductive paste formulation D within the injection portion 4 and the periodontal membrane. Therefore, the detection of the filing of the electric conductive paste formulation D to the apical constriction P is determined by monitoring the resistance to be (6.5 k$\Omega$−R1+R2). Alternatively, the relation between the distance from the periodontal membrane to the electric conductive paste formulation D including conductive metals, or conductive metal oxides and the resistance is previously measured by x-ray photographs, and then the distance from the periodontal membrane may be estimated when the resistance reaches to a certain resistance higher than (6.5 k $\Omega$−R1+R2). As described above, since the present invention uses the paste formulation filled in the root canal as the current probe, once the resistance reaches to the above certain value, it is determined that the filling of the root canal by the paste formulation is completed. The construction described above allows to reduce complexity of the root canal filing and/or injection operation that previously requires duplex steps; measuring the root canal length by the impedance, and next spreading the root canal portion and then inserting the gutta percha point to complete the filling of the root canal. In addition, the detection whether or not the paste formulation is filled within the root canal sufficiently becomes easy whereas such detection is regarded to be difficult in the conventional root canal filling/injection operation. Therefore, the present invention can provide the system for detecting of paste filling which makes the measurement more speedy and easier, and that ensures the filling of the paste formulation.

The power supply 102 used may be selected from a direct current type or an alternative current type, and the value of R2 and the internal resistance etc. may be selected as requested. The measurement etc. may be achieved through the resistance measurement or the impedance measurement depending on the kinds of the power supplies used. It may possible to alarm the operator to pay attention when the predetermined working length is obtained.

Hereafter, the present invention will be explained in detail by examples, however, these examples are provided only for explanation of the present invention and do not intend to limit the scope of the present invention.

EXAMPLES

Example 1

To a solid component including 50 wt % of calcium hydroxyde, iodoform 20 wt %, 30 wt % of silicone oil was added and mixed to prepare a paste formulation.

To this paste formulation, further 10 wt % of a silver powder based on the weight of the above solid component was added and mixed to form the paste formulation according to the present invention. The current of 5 mA was flew in the resulted electric conductive paste formulation as measured by an ampere meter. Next, a lead line having 0.1 mm diameter was inserted to a injection portion of a commercially available paste injector so as to prepare the paste injector according to the present invention as shown in FIG. 3. The electric conductive paste as prepared above was filled in the paste injector, and the paste discharge through the tip portion was confirmed.

Figure 8:
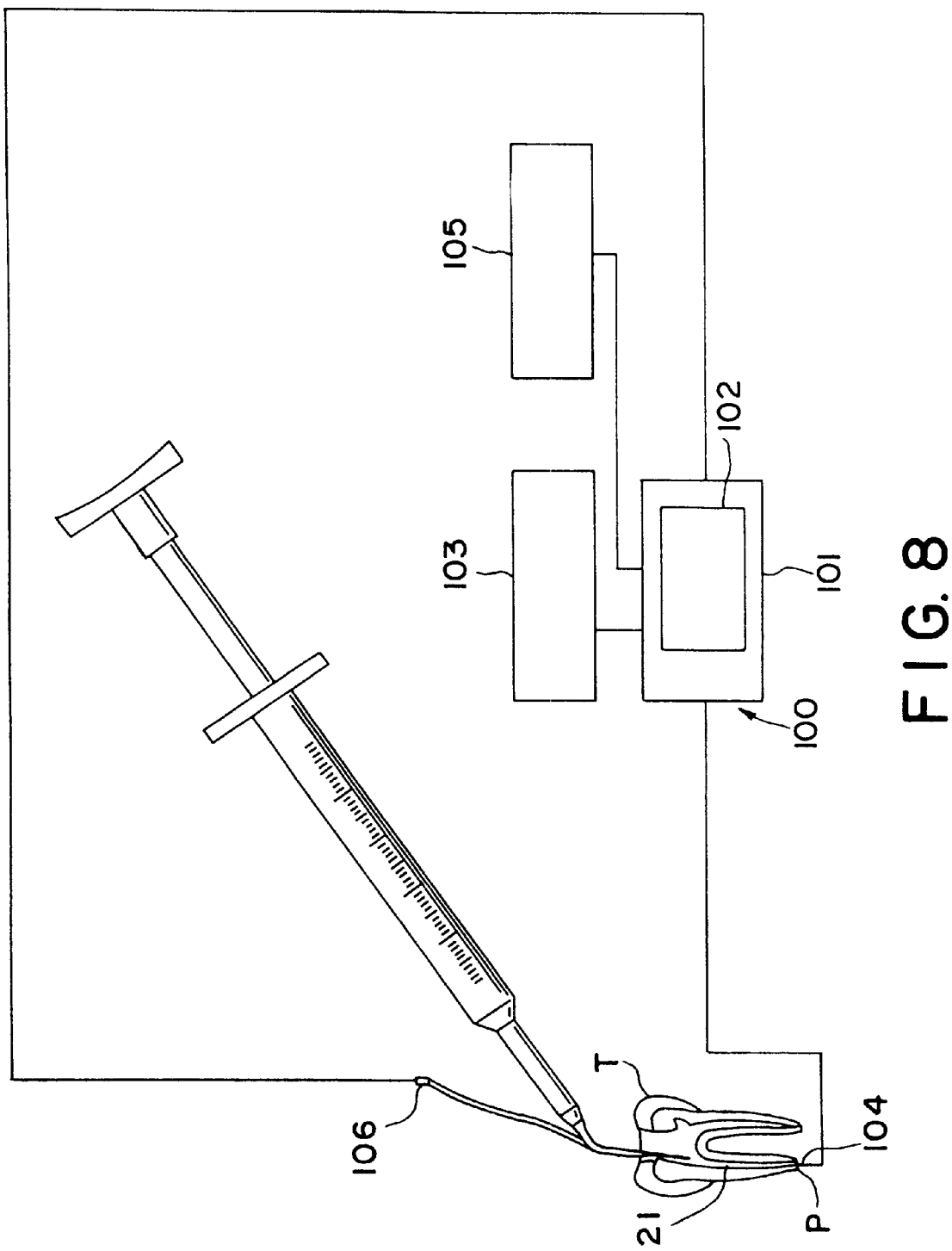
FIG. 8 shows an electric circuit arrangement used for testing the paste according to the present invention.

A circuit illustrated in FIG. 8 was constructed using a pulpless tooth and injecting the electronic conductive paste formulation into the root canal 21 using the paste injector in order to operate the root canal filling. The front end of the electrode 104 of the resistance measurement device 100 was located inside the root canal 21 slightly above the apical constriction P. As the injection of the electric conductive paste formulation was started and was proceeded, the current detector 101 detect the current through the circuit shown in FIG. 8.

Thereafter, the injection portion of the paste injector was pulled out carefully from the pulpless tooth, and an x-ray photograph was taken to observe the filling condition of the electric conductive paste formulation. It was confirmed that the electronic conductive paste formulation reached to the apical constriction P. That is, the detection of the circuit formation by the electronic conductive paste formulation being reached to the apical constriction P indicates the completion of the root canal filling.

Example 2

40 wt % of hydroxy appertite, 10 wt % of barium sulfate, 50 wt % of silicone oil were mixed together to form the paste formulation. Au powder of 25 wt % was mixed to the above paste formulation. The current of 3 mA flew in the resulted paste as measured by the ampere meter. The resulted electric conductive paste formulation was used in the same test as described in the Example 1. It was confirmed that the electric conductive paste was filled in the apical constriction P of the damaged tooth.

Industrial Availibility

As described above, since the present invention uses the paste formulation filled in the root canal as the current probe, the completion of the paste formulation into the root canal is immediately detected when the resistance becomes the above described value. Therefore, conventional duplex procedures comprising measuring the root canal length by the impedance measurement, next spreading the root canal, and then inserting the gutta percha point so as to fill the root canal is not required. In addition, the detection whether or not the paste is entirely filled in the root canal becomes easy, which was difficult in the conventional root canal filling operation using the paste. The present invention may provide the system for detecting of paste filling which is carried out more speedy and easier while ensuring the filling of the paste sufficiently.

The present invention has been explained by non-limiting exemplary examples, however, it is appreciated by a person skilled in the art that many other variations, modifications, and omissions may be possible within the scope of the invention as described in the appended claims. True scope of the present invention will only be limited by the claims.

I claim:

1. A paste injector for dental use comprising:

a container portion for holding an electric conductive paste;

an insert portion inserted into said container portion;

an injection portion for injecting into a constricted portion and having an inner path for guiding said electric conductive paste to said constricted portion, said injection portion being connected to said container portion so as to receive said electric conductive paste pressured by said insert portion, and an electric conductive member for electrically connecting said electrically conductive paste to an external electrode positioned outside said paste injector wherein said electric conductive member comprises a first end extending through said inner path of said injection portion, a second end drawn out of said paste injector, and a lead line connecting between said first end and said second end.

2. The paste injector for dental use according to claim 1, wherein said insert portion has a first end, and said electric conductive member comprises a first terminal exposed at a face of said first end of said insert portion and contacting said electric conductive paste, a second terminal disposed at said insert portion and exposed outside said insert portion so as to electrically connect said electrically conductive paste to an external electrode positioned outside said paste injector, and a lead line connecting between said first terminal and said second terminal.

3. The paste injector for dental use according to claim 2, wherein said lead line of said electric conductive member is inserted through said insert portion between said first end and said second end.

4. A system for detecting paste filling comprising:

a paste injector comprising a container portion for holding a mixed electric conductive paste, said electric conductive paste comprising 5–50 weight % of electric conductive powder based on a solid component of said electric conductive paste, at least one compound selected from the group consisted of calcium hydroxide, hydroxy apatite and tricalcium phosphate, and at least one vehicle selected from the group consisting of silicone oil, guaiacol formaldehyde mixture, propylene glycol, dry ethanol, caster oil, liquid paraffin; an insert portion inserted into said container portion; an injection portion for injecting into a constricted portion and having inner path for guiding said electric conductive paste to said constricted portion, said injection portion being connected to said container portion so as to receive said electric conductive paste pressured by said insert portion; and an electric conductive member for electrically connecting said electrically conductive paste to an external electrode positioned outside said paste injector wherein said electric conductive member comprises a first end extending through said inner path of said injection portion, a second end drawn out of said paste injector, and a lead line connecting between said first end and said second end;

a current detector for detecting current flowing between said electric conductive paste injected into said constricted portion and said external electrode; and a current display device for indicating said current flowing through said electric conductive paste filled into said constricted portion.

* * * * *